US008343217B2

(12) United States Patent
Bumbalough

(10) Patent No.: US 8,343,217 B2
(45) Date of Patent: Jan. 1, 2013

(54) INTRAOCULAR LENS AND METHODS FOR PROVIDING ACCOMMODATIVE VISION

(75) Inventor: Timothy R. Bumbalough, Fullerton, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 108 days.

(21) Appl. No.: 12/849,451

(22) Filed: Aug. 3, 2010

(65) Prior Publication Data

US 2011/0040379 A1 Feb. 17, 2011

Related U.S. Application Data

(60) Provisional application No. 61/230,914, filed on Aug. 3, 2009.

(51) Int. Cl.
*A61F 2/16* (2006.01)
(52) U.S. Cl. ....................................... 623/6.46; 623/6.37
(58) Field of Classification Search ................ 623/6.11, 623/6.37–6.43, 6.46, 6.49, 6.51
See application file for complete search history.

(56) References Cited

U.S. PATENT DOCUMENTS

| | | | |
|---|---|---|---|
| 4,361,913 A | 12/1982 | Streck | |
| 4,370,760 A | 2/1983 | Kelman | |
| 4,373,218 A | 2/1983 | Schachar | |
| 4,442,553 A | 4/1984 | Hessburg | |
| 4,512,040 A | 4/1985 | McClure | |
| 4,560,383 A | 12/1985 | Leiske | |
| 4,562,600 A | 1/1986 | Ginsberg et al. | |
| 4,615,701 A | 10/1986 | Woods | |
| 4,641,934 A | 2/1987 | Freeman | |
| 4,731,078 A | 3/1988 | Stoy et al. | |
| 4,769,035 A | 9/1988 | Kelman | |
| 4,813,955 A | 3/1989 | Achatz et al. | |
| 4,842,601 A | 6/1989 | Smith | |
| 4,888,012 A | 12/1989 | Horn et al. | |

(Continued)

FOREIGN PATENT DOCUMENTS

CH 681687 A5 5/1993

(Continued)

OTHER PUBLICATIONS

English translation of WO 93/05733 A1.

(Continued)

*Primary Examiner* — William H. Matthews
(74) *Attorney, Agent, or Firm* — Abbott Medical Optics Inc.

(57) ABSTRACT

An accommodating intraocular lens for providing a range of accommodative vision contains an optic and a haptic. The optic is disposed about an optical axis and includes an anterior surface and a posterior surface defining a clear aperture of the optic. The haptic is at least partially disposed inside the optic and includes an inner structure, an outer structure, and a plurality of arms disposed between and connecting the inner structure and the outer structure. The inner structure is circumferentially disposed about the optical axis, while the outer structure is circumferentially disposed about the inner structure and has an outer face. Each arm has proximal portion adjacent the inner structure and a distal portion adjacent the outer structure that is bifurcated in a radial direction from the proximal portion. The intraocular lens also has an outer surface defined by outer surfaces of the plurality of arms and an outer surface of the outer structure. The inner structure and at least a portion of the arms are disposed inside the clear aperture. The distal portion of each arm has a larger axial extent than an axial extent of the inner portion. The distal portion of each arm has a larger axial extent along the outer surface than an axial extent of the outer structure along the outer surface.

4 Claims, 6 Drawing Sheets

U.S. PATENT DOCUMENTS

| | | | |
|---|---|---|---|
| 4,892,543 | A | 1/1990 | Turley |
| 4,932,966 | A | 6/1990 | Christie et al. |
| 4,932,968 | A | 6/1990 | Caldwell et al. |
| 4,963,148 | A | 10/1990 | Sulc et al. |
| 4,994,082 | A | 2/1991 | Richards et al. |
| 4,994,083 | A | 2/1991 | Sulc et al. |
| 5,047,051 | A | 9/1991 | Cumming |
| 5,152,789 | A | 10/1992 | Willis |
| 5,275,623 | A | 1/1994 | Sarfarazi |
| 5,476,514 | A | 12/1995 | Cumming |
| 5,489,302 | A | 2/1996 | Skottun |
| 5,496,366 | A | 3/1996 | Cumming |
| 5,607,472 | A | 3/1997 | Thompson |
| 5,628,795 | A | 5/1997 | Langerman |
| 5,674,282 | A | 10/1997 | Cumming |
| 5,984,962 | A | 11/1999 | Anello et al. |
| 6,013,101 | A | 1/2000 | Israel |
| 6,051,024 | A | 4/2000 | Cumming |
| 6,083,261 | A | 7/2000 | Callahan et al. |
| 6,110,202 | A | 8/2000 | Barraquer et al. |
| 6,117,171 | A | 9/2000 | Skottun |
| 6,120,538 | A | 9/2000 | Rizzo, III et al. |
| 6,197,059 | B1 | 3/2001 | Cumming |
| 6,200,342 | B1 | 3/2001 | Tassignon |
| 6,217,612 | B1 | 4/2001 | Woods |
| 6,299,641 | B1 | 10/2001 | Woods |
| 6,443,985 | B1 | 9/2002 | Woods |
| 6,930,838 | B2 | 8/2005 | Schachar |
| 7,097,660 | B2 | 8/2006 | Portney |
| 7,150,759 | B2 | 12/2006 | Paul et al. |
| 7,179,292 | B2 | 2/2007 | Worst et al. |
| 7,220,279 | B2 | 5/2007 | Nun |
| 7,503,938 | B2 | 3/2009 | Phillips |
| 7,815,678 | B2 | 10/2010 | Ben Nun |
| 2003/0004569 | A1 | 1/2003 | Haefliger |
| 2004/0082993 | A1 | 4/2004 | Woods |
| 2004/0082995 | A1 | 4/2004 | Woods |
| 2004/0111153 | A1 | 6/2004 | Woods et al. |
| 2005/0018504 | A1 | 1/2005 | Marinelli et al. |
| 2005/0021139 | A1 | 1/2005 | Shadduck |
| 2005/0131535 | A1 | 6/2005 | Woods |
| 2006/0238702 | A1 | 10/2006 | Glick et al. |
| 2007/0078515 | A1 | 4/2007 | Brady |
| 2007/0100444 | A1 | 5/2007 | Brady et al. |
| 2007/0106381 | A1 | 5/2007 | Blake |
| 2007/0129798 | A1 | 6/2007 | Chawdhary |
| 2007/0135915 | A1 | 6/2007 | Klima |
| 2007/0213817 | A1 | 9/2007 | Esch et al. |
| 2007/0260309 | A1 | 11/2007 | Richardson |
| 2008/0161913 | A1 | 7/2008 | Brady et al. |
| 2008/0161914 | A1 | 7/2008 | Brady et al. |
| 2009/0012609 | A1 | 1/2009 | Geraghty et al. |

FOREIGN PATENT DOCUMENTS

| | | |
|---|---|---|
| EP | 766540 A1 | 4/1997 |
| EP | 766540 B1 | 8/1999 |
| JP | 2126847 | 5/1990 |
| WO | WO0119288 A1 | 3/2001 |
| WO | WO0219949 A2 | 3/2002 |
| WO | WO2005115278 A1 | 12/2005 |

OTHER PUBLICATIONS

U.S. Appl. No. 09/656,661, filed Sep. 7, 2000.
Thornton S., "Accommodation in Pseudophakia," 1991, pp. 159-162.
U.S. Appl. No. 09/721,072, filed Nov. 22, 2000.

INTRAOCULAR LENS AND METHODS FOR PROVIDING ACCOMMODATIVE VISION

CLAIM OF PRIORITY

The present application claims priority under 35 U.S.C §119(e) to provisional application No. 61/230,914, filed on Aug. 3, 2009 under the same title, which is incorporated herein by reference in its entirety. Full Paris Convention priority is hereby expressly reserved.

BACKGROUND OF THE INVENTION

1. Field of the Invention

The present invention relates generally to intraocular lenses, and more specifically to intraocular lenses for providing accommodative vision to a human or animal subject.

2. Description of the Related Art

A human eye can suffer diseases that impair a person's vision. For instance, a cataract may increase the opacity of the lens, causing impaired vision or blindness. To restore the patient's vision, the diseased lens may be surgically removed and replaced with an artificial lens, known as an intraocular lens (IOL). An IOL may also be used for presbyopic lens exchange.

The simplest IOLs have a single fixed focal length, or, equivalently, a single fixed power. Unlike the eye's natural lens, which can adjust its focal length and/or axial location within a particular range in a process known as accommodation, these single focal length IOLs cannot generally accommodate. As a result, distant objects may appear in focus, while objects at closer distances appear blurred.

An improvement over fixed, single focal length IOLs is an accommodating IOL (AIOL), which can move axially and/or adjust its optical power within a particular range. As a result, the patient can clearly focus on objects in a range of distances away from the eye, rather than at a single distance. This ability to accommodate is of tremendous benefit for the patient, and more closely approximates the patient's natural vision than a single focal length IOL.

When the eye focuses on a relatively distant object, the lens power is at the low end of the accommodation range, which may be referred to as the "distant" or "far" power. When the eye focuses on a relatively close object, the lens power and/or position is at the high end of the accommodation range, which may be referred to as the "near" power. The accommodation range or add power, as used herein, is defined as the actual or effective near power provided by a lens or optic (e.g., the natural lens or the optic of an IOL) minus the far power provided by the lens or optic. In general, an accommodation range of 2 to 4 Diopters is considered sufficient for most patients.

The human eye contains a structure known as the capsular bag, which surrounds the natural lens. The capsular bag is transparent, and serves to hold the lens. In the natural eye, accommodation is initiated by the ciliary muscle and a series of connective fibers known as zonules. The zonules are located in a relatively thick band mostly around the equator of the lens, and impart a largely radial force to the capsular bag that can alter the shape and/or the location of the natural lens and thereby change its actual or effective power.

In a surgery in which the natural lens is removed from the eye, a small opening is typically made in the front of the capsular bag through which lens material is typically broken up and vacuumed out of the eye, the rest of the capsular bag being left intact. The remaining capsular bag may be extremely useful for an accommodating intraocular lens, in that the eye's natural accommodation is initiated at least in part by an ocular force produced by the ciliary muscle, zonules, and/or capsular bag. The capsular bag may be used to house an accommodating IOL, which in turn can change shape or optical power of the IOL, and/or shift or axially move the optic of the IOL in some manner to affect the location of the image plane of the optic.

In general, the IOL includes an optic, which refracts and/or diffracts light that passes through it and forms an image on the retina, and a haptic or support structure, which mechanically couples the optic to the capsular bag. During accommodation, the zonules exert a force on the capsular bag, which in turn exerts a force on the optic. The force may be transmitted from the capsular bag directly to the optic, or from the capsular bag through a haptic to the optic.

A desirable optic for an accommodating IOL is one that changes shape or axially moves in response to an ocular force produced by a squeezing or expanding radial force applied largely to the equator of the optic (e.g., by pushing or pulling on or near the edge of the optic, circumferentially around the optic axis). Under the influence of an ocular force, the optic may bulge slightly in the axial direction, producing more steeply curved anterior and/or posterior faces, and produce an increase in the power of the optic. Likewise, an expanding radial force may produce a decrease in the optic power by flattening the optic. This change in power is accomplished in a manner similar to that of the natural eye.

One challenge in providing an effective AIOL is that of effectively transferring a limited amount of ocular force available from the ciliary muscle or capsular bag of an eye to the optic of the AIOL. Typically, the available ocular force is transferred through a haptic or support structure that absorbs a certain amount of the available energy provided by the ocular force. There is a need to provide haptic or support structures in AIOLs that reduce the amount of energy transferred to that structure so that more of the available force may be converted to changing the shape and/or axial position of the optic portion of the AIOL.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

Figure 1:
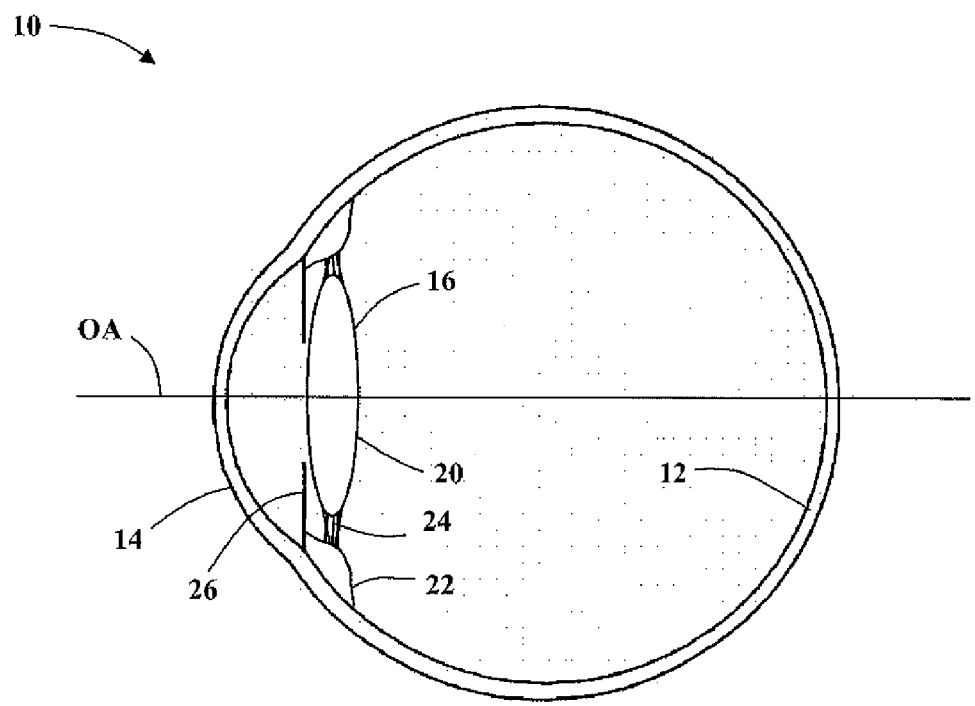
FIG. 1 is a plan drawing of a human eye with a natural lens.

Referring to FIG. 1, an eye 10 is illustrated that includes a retina 12 for receiving an image produced by a cornea 14 and a natural lens 16 from light incident upon eye 10. Natural lens 16 is disposed within a capsular bag 20 which separates anterior and posterior chambers of eye 10. Capsular bag 20 is made of a resilient material that changes the shape and/or location of natural lens 16 in response to ocular forces produced when ciliary muscle 22 contracts and stretches natural lens 16 via zonules 24 disposed about an equatorial region of capsular bag 20. This action flattens natural lens 16, thereby producing a relatively low optical power for providing distant vision in an emmetropic eye. To produce intermediate and/or near vision, ciliary muscle 22 relaxes, thereby relieving tension on zonules 24. The resiliency of capsular bag 20 provides an ocular force that reshapes natural lens 16 to increase its curvature and provide a relatively high optical power suitable for intermediate and/or near vision.

Figure 2:
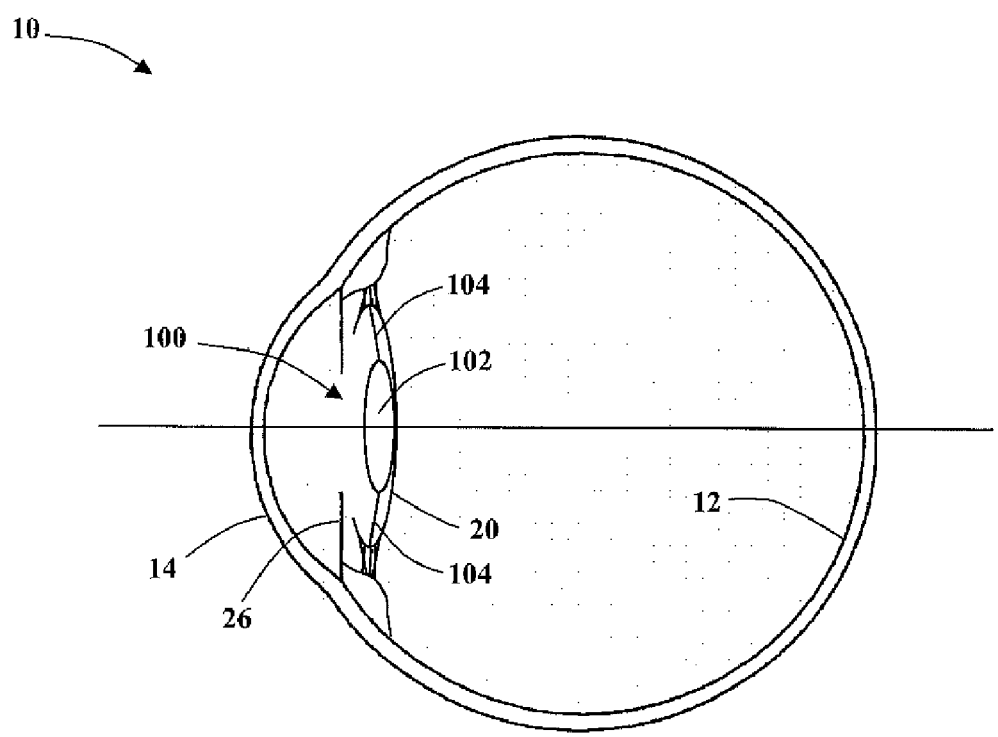
FIG. 2 is a plan drawing of a human eye with an intraocular lens.
Figure 3:
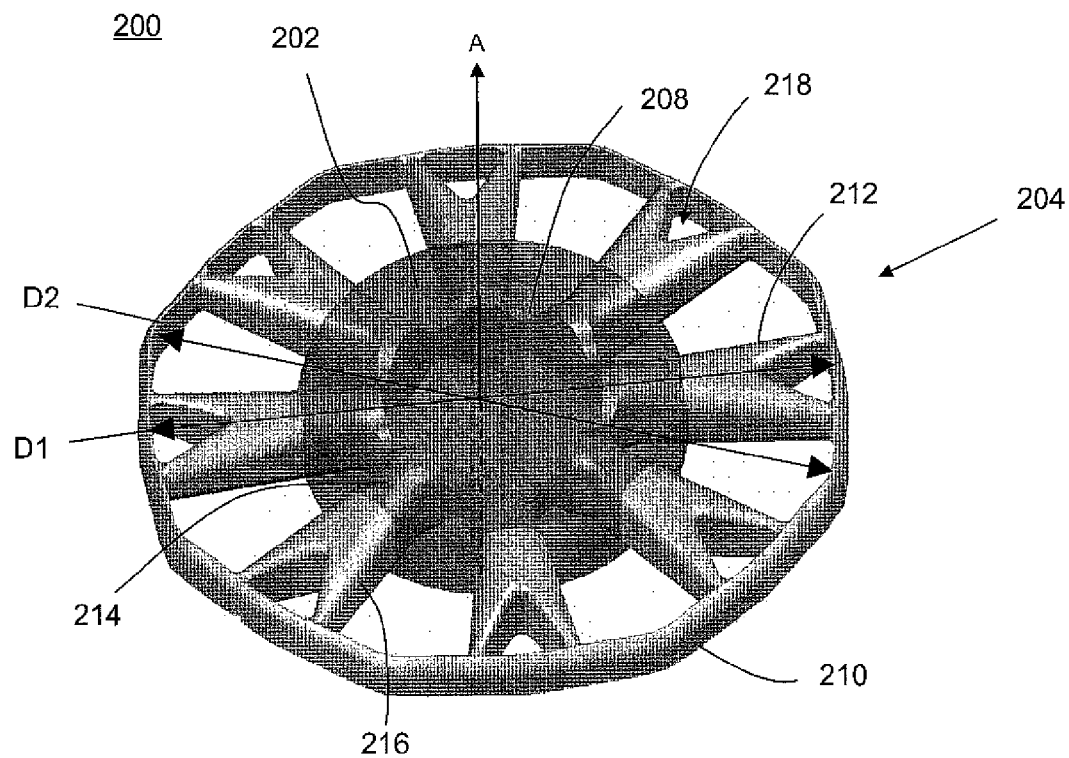
FIG. 3 is a perspective view of an intraocular lens embodying features of this invention.
Figure 4:
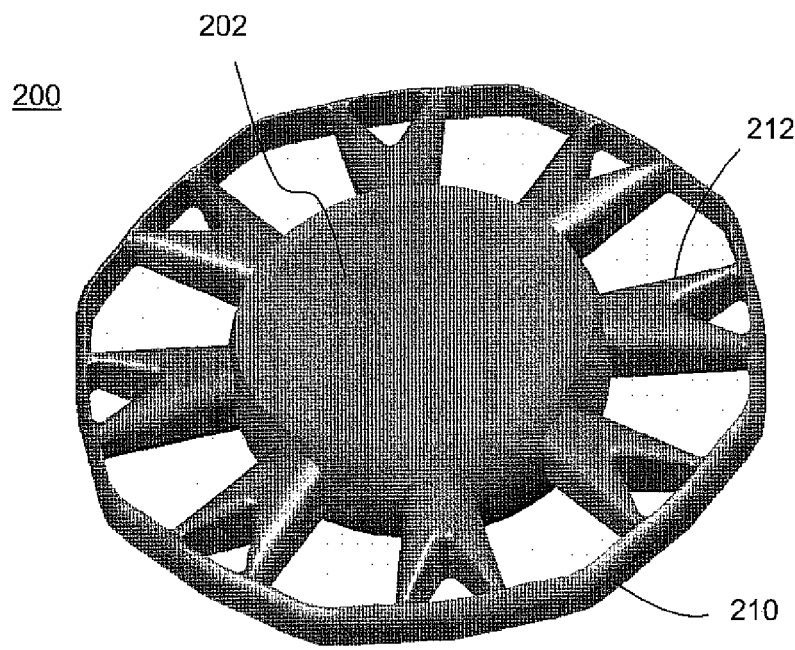
FIG. 4 is a perspective view of an intraocular lens embodying features of this invention.

Referring to FIG. 2, natural lens 16 may be removed either in a refractive lens exchange or due to a disease such as cataracts. Natural lens 16 is generally removed via an opening in the anterior wall of the capsular bag 20 (a so called "capsulorhexis"). Natural lens 16 may then be replaced by an IOL or AIOL 100 to provide vision to the subject. IOL 100 includes optic 102 for forming an image on the retina and haptics or support structure 104 for centering optic 102 and, in the case of an AIOL, transferring ocular forces from ciliary muscle 22, zonules 24, and/or capsular bag 20 to optic 102 to changes its shape, power, and/or axial location relative to the retina 12.

Referring to FIGS. 3-6, an AIOL 200 according to an embodiment of the present invention is shown disposed about an optical axis A. AIOL 200 comprises an optic 202 and a haptic or support structure 204 configured to effectively transfer an ocular force from a human or animal eye to the optic 202 so as to produce a range of powers in response to the ocular force. Haptic 204 includes an inner structure 208 and outer structure 210 and a plurality of arms 212 connecting or coupling structures 208, 210 to one another in a way that efficiently and effectively transfers ocular forces. Haptic 204 thus changes the shape and/or axial location of the optic 202, thereby providing a change in optic power and/or focal plane location of optic 202. Arms 212 each include a proximal end 214 coupled or connected to inner structure 208 and distal end 216 coupled or connected to outer structure 210.

Optic 202 may be molded directly onto haptic 204. Alternatively, optic 202 may be formed or fabricated separately from haptic 204, and then attached to haptic 204. In certain embodiments, haptic 204 is first machined or molded, and then optic 202 is molded and/or machined over or on top of haptic 204.

Optic 202 is preferably made from a relatively soft material, so that it can deform or change shape readily under the limited deforming forces produced by the capsular bag and/or ciliary muscle. An exemplary material is a relatively soft silicone material, although other suitable materials may be used as well. The stiffness of optic 202 may be less than 500 kPa, preferably from 0.5 kPa to 500 kPa. In some embodiments, the stiffness of optic 202 is between 25 kPa and 200 kPa or between 25 kPa and 50 kPa.

In contrast with optic 202, at least portions of haptic 204 (e.g., arms 212) are generally made of a relatively stiffer material than optic 202 material, so that haptic 204 can efficiently transmit ocular forces to optic 202. An exemplary material is a relatively stiff silicone material, although other suitable materials may be used as well, such as acrylic, polystyrene, or clear polyurethanes. The stiffness of haptic 204 may be greater than or equal to 500 kPa, or greater than or equal to 3000 kPa.

Arms 212 protrude or extend into optic 202 that include the clear aperture of optic 202. As used herein, the term "clear aperture" means the area of a lens or optic that restricts the extent of a bundle of rays from a collimated source or a distant light source that can imaged or focused by the lens or optic. The clear aperture is usually circular and is specified by its diameter. In some embodiments, the clear aperture has the same or substantially the same diameter as the optic. Alternatively, the diameter of the clear aperture may be smaller than the diameter of the optic, for example, due to the presence of a glare or PCO reducing structure disposed about a peripheral region of the optic.

Since inner structure 208 and the proximal ends 214 of arms 212 are located inside optic 202 and within the clear aperture thereof, at least these portions of haptic 204 are beneficially transparent or nearly transparent, so that it does not substantially block or scatter any light transmitted through optic 202. In addition, these portions of haptic 204 may have a refractive index that matches the refractive of optic 202 material so that interfaces between optic 202 and haptic 204 do not produce significant reflections or refractions that might produce scattered light within the eye, which might appear as a glare or haze to the patient.

A numerical example may be used to illustrate the effect of mismatch of refractive indices on reflected power. For a planar interface at normal incidence between air (refractive index of 1) and glass (refractive index of 1.5), 4% of the incident power is reflected at the interface. For such an interface between air and glass, there is no attempt to match refractive indices, and this 4% reflection will merely provide a baseline for comparison. If, instead of 1 and 1.5, the refractive indices differ by 4%, such as 1.5 and 1.56 or 1.5 and 1.44, there is a 0.04% reflection, or a factor of 100 improvement over air/glass. Finally, if the refractive indices differ by only 0.3%, such as 1.5 and 1.202 or 1.5 and 1.495, there is a 0.00028% reflection, or a factor of over 14000 improvement over air/glass. In practice, tolerances such as the 0.3% case may be achievable, and it is seen that a negligible fraction of power may be reflected at the interface between a haptic and an optic whose refractive indices differ by 0.3%. Note that the above base value of 1.5 was chosen for simplicity, and that haptic 204 and optic 202 may have any suitable refractive index.

Thus, the refractive indices of optic 202 and at least portions of haptic 204 inside optic 202 are equal or essentially the same. For the purposes of this document, "essentially the same" means that their refractive indices are equal to each other at a wavelength within the visible spectrum (i.e., between 400 nm and 700 nm). Note that haptic 204 and optic 202 may optionally have different dispersions, where the refractive index variation, as a function of wavelength, may be different for the haptic and the optic. In other words, if the refractive indices of haptic 204 and optic 202 are plotted as a function of wavelength, they may or may not have different slopes, and if the two curves cross at one or more wavelengths between 400 nm and 700 nm, then the refractive indices may be considered to be essentially the same or essentially equal.

The extension of arms 212 into optic 202 generally allows more effective transfer of radial forces along arms 212 to optic 202, since the inner diameter of inner structure 208 is less than the overall or outer diameter of optic 202. The relatively small "active area" of optic 202 located inside inner structure 208 allows ocular forces to be distributed over a smaller peripheral zone about the active area than if the same force were distributed over a periphery of the outer diameter, or a larger diameter, of optic 202. Since ocular forces are effectively concentrated over a relatively small area in the illustrated embodiment, this increases the pressure near the center of optic 202, which in turn increase the amount of curvature change or optical power change induced for a given amount of radial force on outer structure 210 and arms 212. As a result, the limited ciliary muscle or capsular bag force may produce a greater accommodative power change and/or axial translation optic 202. As used herein the term "active area" of an optic means a pupil of an optic over which a clinically significant change in optical power occurs in reaction to an ocular force generally sufficient to produce near vision in a human eye (e.g., an ocular force of 10 grams force).

The inner diameter of inner structure 208 is generally selected to be at least large enough that the active area of optic 202 can provide a change in optical power under scotopic lighting conditions (e.g., with a pupil diameter of the eye of 2 millimeters to 3 millimeters). For example, when intraocular lens 200 is used in a human eye, the active area is generally sufficiently large when the inner diameter of inner structure 208 is between 2 millimeters and 4 millimeters, or between 2.5 millimeters and 3.5 millimeters, or 3 millimeters plus or minus 0.25 millimeters.

In some embodiments, the axial thickness of inner structure 208 portion between arms 212, and/or overlapping proximal ends 214, is relatively large, for example, to help distribute more radial force on outer structure 210 into forces that change the shape of the anterior and posterior surfaces of optic 202. In some embodiments, the ratio of the optic center thickness to the axial thickness of inner structure 208 is less than or equal to 2. In other embodiments, greater accommodative power change in optic 202 is provided when the ratio of the optic center thickness to the axial thickness of inner structure 208 is less than 1.8 or less than 1.5.

Inner structure 208 may be in the form of a continuous ring and may generally have a radial thickness that is from 0.1 millimeters to 0.2 millimeters or of about 0.15 millimeters (e.g., 0.15 millimeters plus or minus 0.03 millimeters). While the continuous ring form of inner structure 208 favorably helps to maintain the figure of optic 202 when deformed during accommodation, it has been discovered that a relatively small radial thickness of inner structure 208 reduces the stiffness of inner structure 208, so that more of the radial forces transferred from arms 212 and are focused on changing the shape and accommodative optical power of optic 202. In some embodiments, outer structure 210 is broken at predetermined locations.

Figure 6:
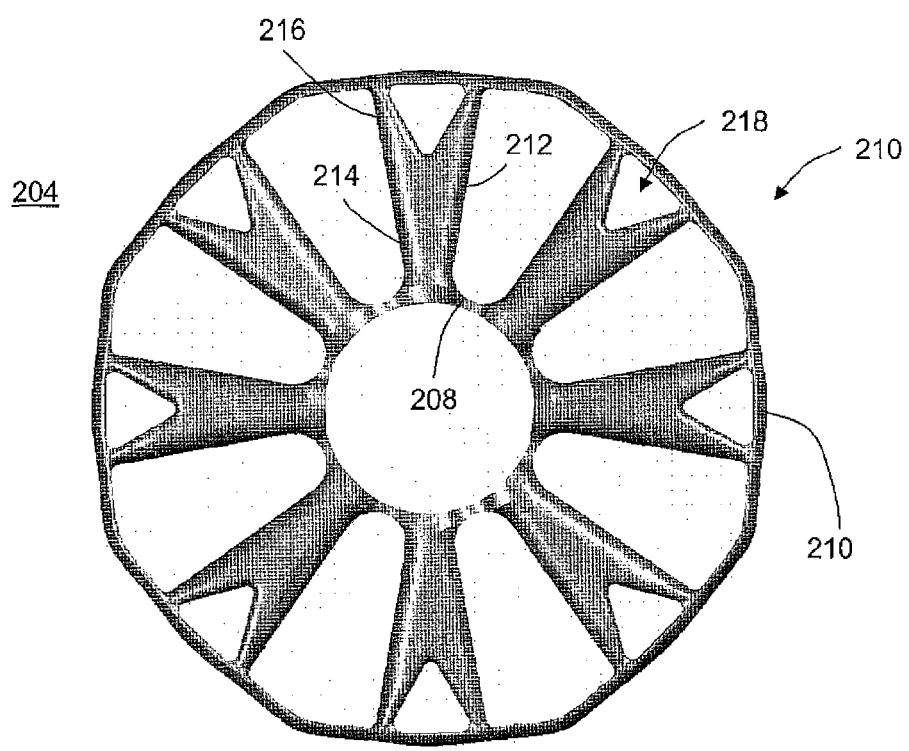
FIG. 6 is a top plan view of a haptic embodying features of this invention.
Figure 7:
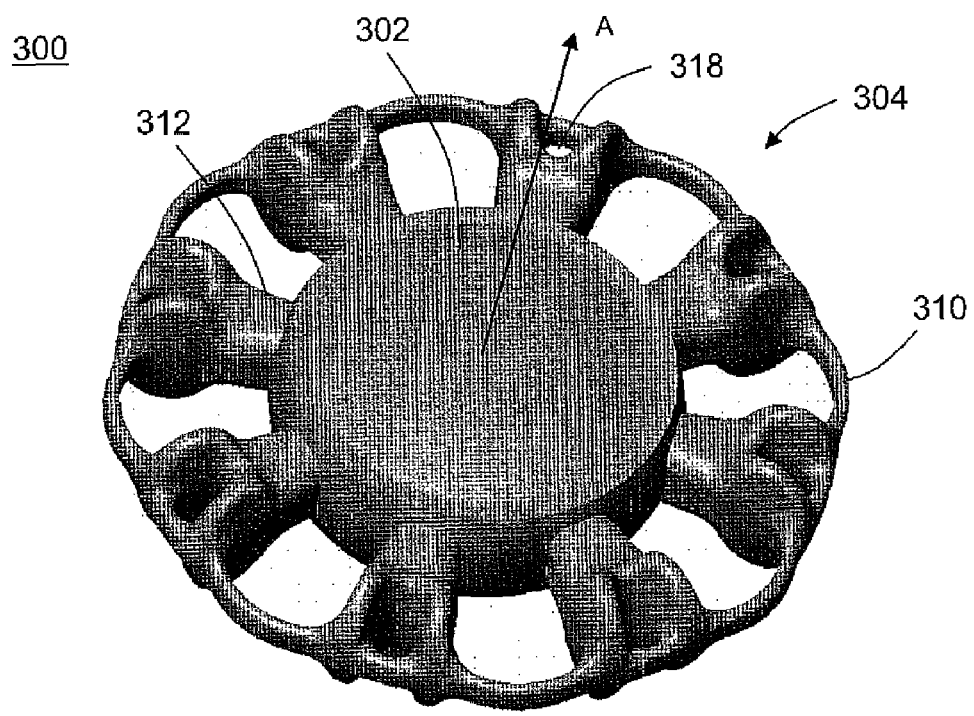
FIG. 7 is a perspective view of an intraocular lens embodying features of this invention.
Figure 8:
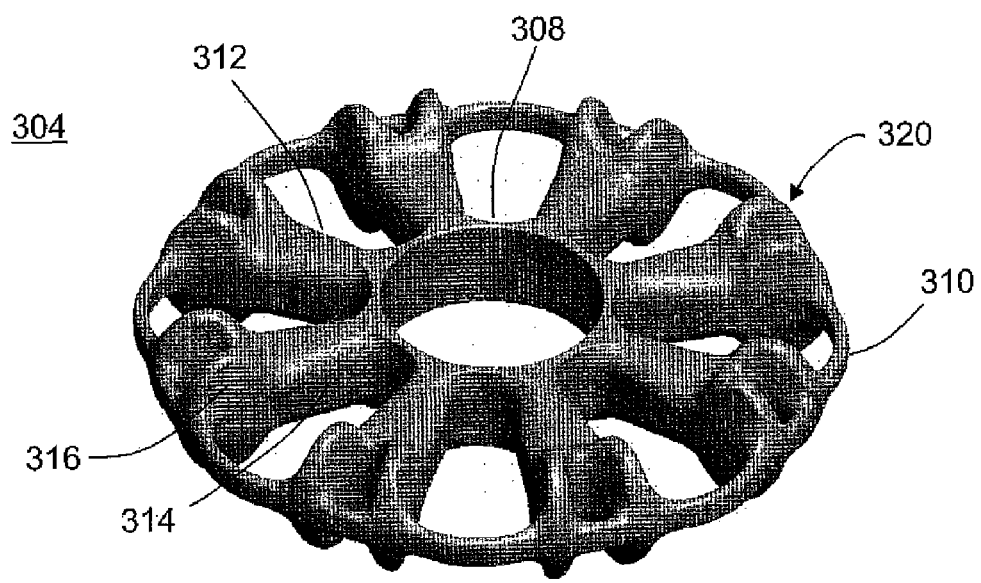
FIG. 8 is a perspective view of a haptic embodying features of this invention.
Figure 9:
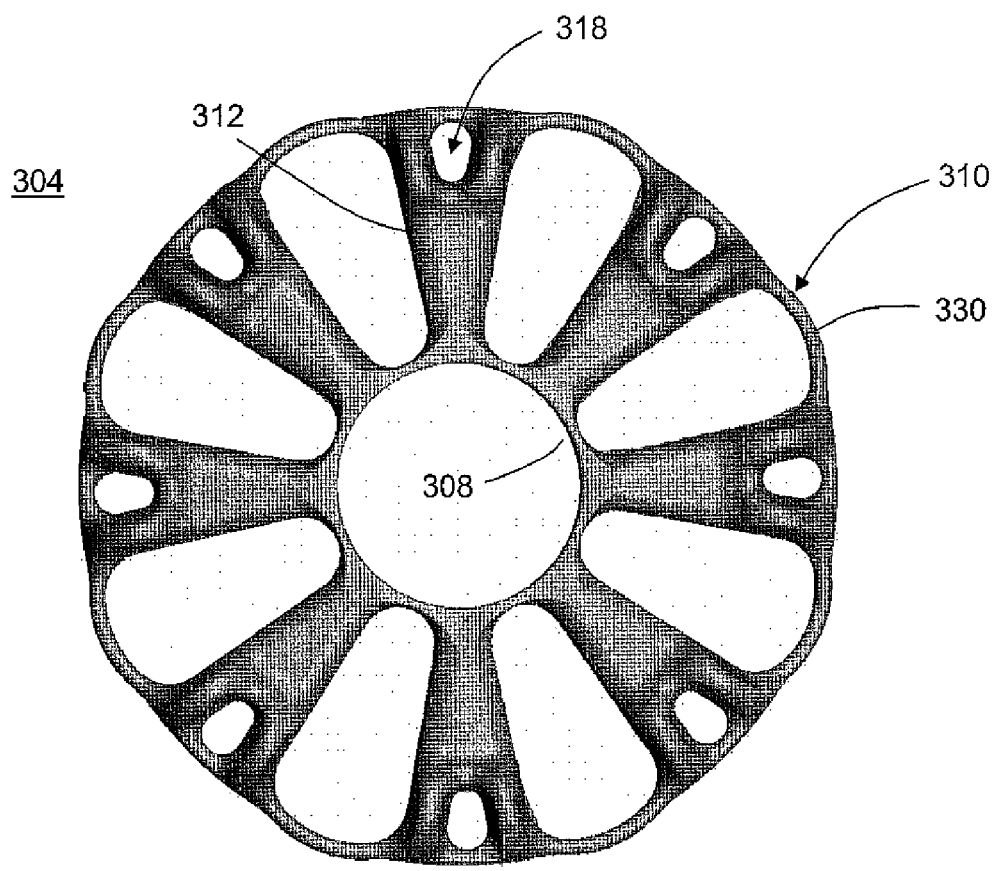
FIG. 9 is a perspective view of a haptic embodying features of this invention.

As seen in FIG. 6, arms 212 may be bifurcated or split at their distal ends 216 to form openings 218. Openings 218 may have a triangular shape, as shown in the illustrated embodiment. Alternatively openings 218 may have a different shape, for example, an oval shape (e.g., see. FIG. 9). Opening 218 may be configured to reduce the mass of haptic 204, help direct radial forces toward inner structure 208, and/or control the shape of outer structure 210 during accommodation (e.g., help avoid bending or buckling). In some embodiments, some or all openings 218 are replaced regions of reduced axial thickness relative to a characteristic axial thickness of the remaining portions of arms 212. In other embodiments, outer structure 210 is either broken in the regions of openings 218 or has a reduced axial thickness relative to the axial thickness of the remaining portions of outer structure 210.

Outer structure 210 of haptic 204 mechanically couples intraocular lens 200 to capsular bag 20. Outer structure 210 may be in the form of a continuous ring and may generally have an axial thickness that is large enough to engage the equatorial region of capsular bag 20 over an area that is large enough to prevent tearing of the bag and to effectively couple ocular forces produced by capsular bag 20 to optic 202. In this regard, outer structure 210 may have an axial thickness that is from 0.5 millimeters to 1.0 millimeters or about 0.75 millimeters (e.g., 0.75 millimeters plus or minus 0.10 millimeters). In some embodiments, outer structure 210 has a radial thickness that is from 0.1 millimeters to 0.2 millimeters or about 0.15 millimeters (e.g., 0.15 millimeters plus or minus 0.03 millimeters). While the continuous ring form of outer structure 210 favorably helps to prevent buckling of AIOL 200, it has been discovered that a relatively small radial thickness reduces the stiffness of outer structure 210 so that radial forces are more effectively transferred along arms 212 and into the active area of optic 202.

Figure 5:
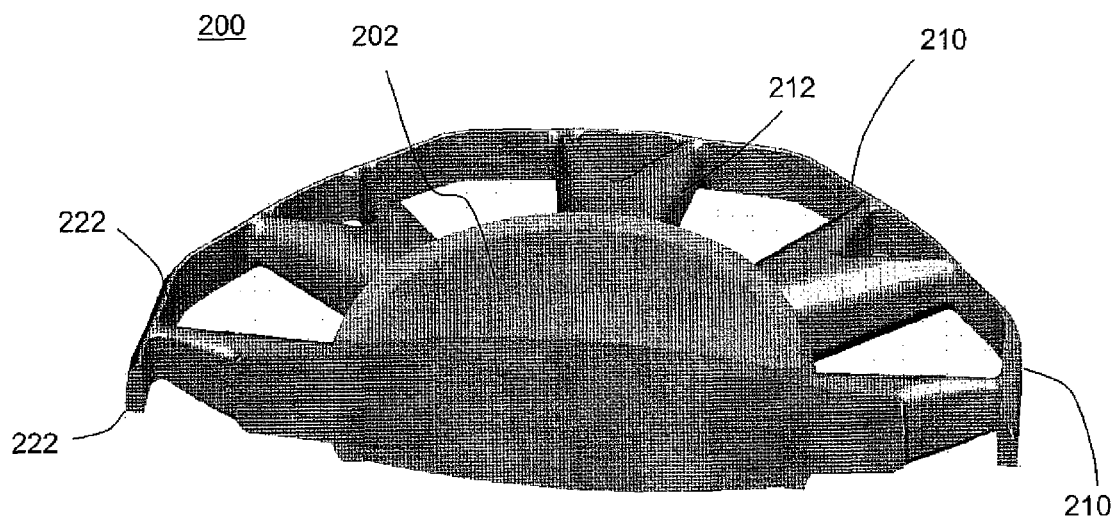
FIG. 5 is a cross sectional view of an intraocular lens embodying features of this invention.

Referring to FIG. 5, at least one of the edges of outer structure may have a discontinuity or sharp edge corner 222, for example, to help prevent PCO. Generally, sharp edge corner 222 has a radius that is less than 500 nanometers, preferably less than 200 nanometers. Additionally or alternatively, the side wall of optic 202 intersects the anterior face or posterior face of optic 202 to form a discontinuity or sharp edge corner that generally has a radius of curvature that is less than 500 nanometers, preferably less than 200 nanometers.

Outer structure 210 may be configured to have two outer diameters D1, D2, where D2 is greater than D1. In the illustrated embodiment, D1 is the outer diameter of outer structure 210 along opposite pairs of arms 212, while D2 is the outer diameter of outer structure 210 between adjacent pairs of arms 212. D1, D2 are advantageously selected to allow the AIOL 200 to accommodate a range of capsular bag sizes that is generally superior to a substantially equivalent outer structure that is circular or even oval in shape, or that includes indents that protrude inwardly toward the center of the intraocular lens. For example, the larger diameter D2 provides for at least portions of a capsular bag having a diameter of, or about equal to, D2 to contact the outer structure 210 when the eye is in a disaccommodative state, whereby accommodative forces may be effectively transmitted to optic 202. Alternatively, if the capsular bag has a diameter of, or about equal to, D1, then the capsular bag will contact the outer structure about its entire circumference. The capsular bag may be slightly taut over portions of ring 202 having the diameter D2, but the overall stress on the capsular bag is less than that experienced for a ring having a constant outer diameter of D2. Accordingly, the outer structure 210 of AIOL 200 is favorably configured to accommodate a larger variation of bag sizes than a substantially equivalent intraocular lens having an outer structure with a constant outer diameter. In certain embodiments, the outer diameter D2 is between 20 microns and 500 microns greater than the outer diameter D1, preferably between 40 microns and 250 microns greater than the outer diameter D1.

In certain embodiments, optic 202 is a multifocal optic, changes from a monofocal optic to a multifocal optic, depending upon the amount of ocular force on haptic 204 and/or the state of accommodation of the eye into which AIOL 200 is inserted.

Referring to FIGS. 7-11, an AIOL 300 according to an embodiment of the present invention is shown that comprises an optic 302 and a haptic or support structure 304 configured to effectively transfer an ocular force from a human or animal eye to optic 302 so as to produce a range of powers in response to an ocular force. Haptic 304 includes an inner structure 308 and an outer structure 310 and a plurality of arms 312 connecting or coupling structures 308, 310 to one another so as to efficiently and effectively transfer the ocular force to changing the shape and/or axial location of optic 302, thereby providing a change in optic power and/or focal plane location of optic 302. Arms 312 each include a proximal end 314 coupled or connected to inner structure 308 and distal end 316 coupled or connected to outer structure 310.

AIOL 300 is similar to AIOL 200 in many ways; however, also includes design features that are configured alter the way in which forces are transferred from haptic 304 to optic 302, or to otherwise alter performance and/or function. Where appropriate, structures and features of AIOL 200 discussed above may be incorporated into AIOL 300. For example, AIOL 300 may be made of the same or similar materials as those discussed for AIOL 200. Except where indicated otherwise, dimensions of AIOL 200 may be incorporated into embodiments according to AIOL 300 (e.g., the thickness or other dimensions of inner structure 308 may be the same or similar to those illustrated and discussed for inner structure 208; the shape and/or size of at least portions of arms 312 may be the same or similar to those illustrated and discussed for arms 212; and the like).

Arms 312 have a general shape that is similar to that of arms 212 of haptic 202, for example, including a bifurcated distal ends 316. Outer structure 310 comprises a series of arcuate ribbons 330 connecting individual arms 312 to one another. In the illustrated embodiment, ribbons 330 curve outwardly away from optical axis OA, so that portions of ribbons 330 between arms 312 are disposed at a greater radial distance from optical axis OA than portions of ribbons 330 that are coupled or connected to arms 312. Distal ends 316 of arms 312 generally bulge axially compared to the proximal end 314. Distal ends 316 of arms 312 are also curvaceous and void of sharp edges or discontinuities. In order to reduce PCO, the anterior and posterior faces of optic 302 contain sharp edges, similar or equal to those described above with regard to optic 202.

Figure 10:
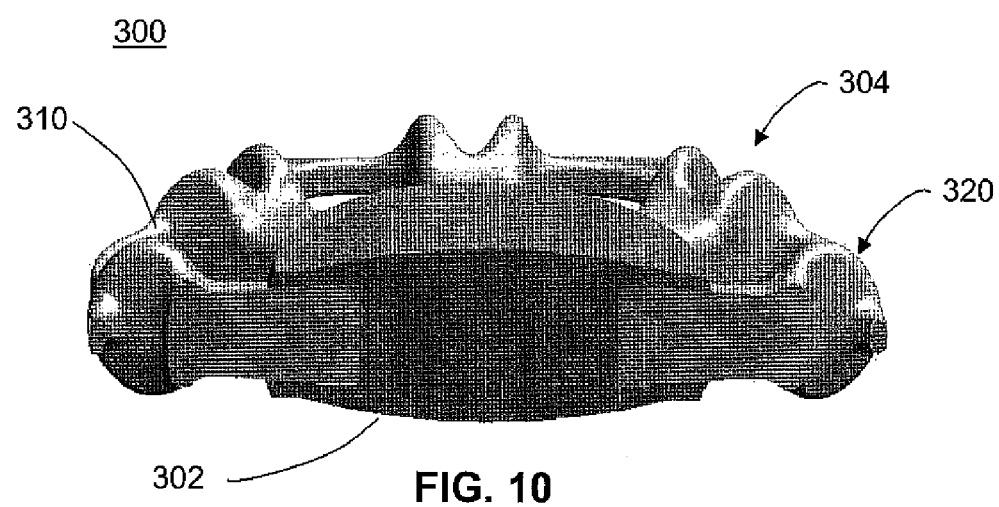
FIG. 10 is a cross sectional view of an intraocular lens embodying features of this invention.
Figure 11:
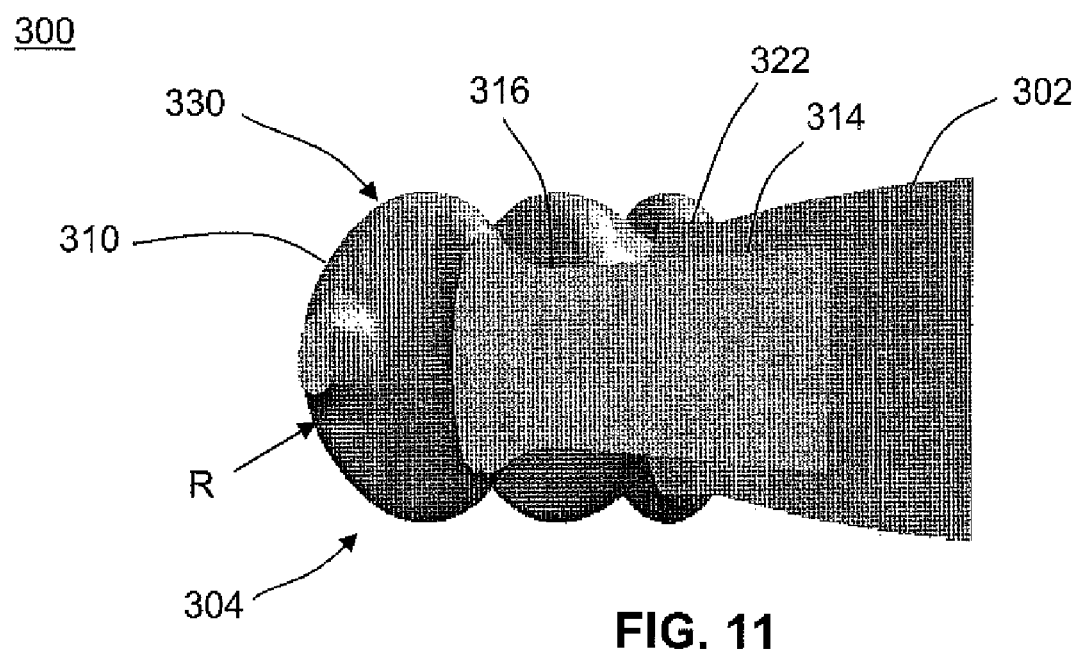
FIG. 11 is a cross sectional view of a portion of an intraocular lens embodying features of this invention.

Referring to FIGS. 10 and 11, outer structure 310 notably has a peripheral region 320 that is generally arcuate in cross-section, for example, to engage a larger portion of the capsular bag than outer structure 210 of AIOL 200. In some embodiments, outer structure 310 has an axial thickness in the vicinity of peripheral region 320 that is from 1.8 millimeters to 2.2 millimeters or about 2.0 millimeters (e.g., 2 millimeters plus or minus 0.1 millimeters). It has been discovered that the relatively large axial thickness of peripheral region 320 (or, large axial extent measured as the distance of the portion of the arm along an axis that is normal to the optical axis) is effective in transferring much of the forces produced by capsular bag 20 and/or zonules 24, since capsular bag 20 is engaged over a large axial extent. Thus, outer structure 310 engages a large extent or area of capsular bag 20, while also providing skeletal structure with a relatively low mass. The low mass of outer structure 310 results in a relatively low stiffness, thus allowing it to conform to changes in the shape of capsular bag 20 during accommodation. This, in turn, allows more of the forces produced by the changing shape of capsular bag 20 to be coupled into haptic 304 and transferred into changing the shape and optical power of optic 302.

Peripheral region 320 has an arcuate shape in a plane parallel to, and passing through, the optical axis OA that is convex. The arcuate shape is characterized by a radius of curvature R. In certain embodiments, radius of curvature R is equal to a radius of curvature of an average capsular bag of a population. For example, radius of curvature R may be 1.13 millimeters plus or minus 0.02 millimeters. In certain embodiments, radius of curvature R is greater than a radius of curvature of an average capsular bag of a population. For example, radius of curvature R may be 1.16 millimeters plus or minus 0.02 millimeters or greater than 1.16 millimeters. A radius of curvature of a peripheral region of haptic 204 may be similarly configured.

Referring to FIG. 11, in some embodiments, the relatively thick optic 302 (or optic 202 of IOL 200) comprises a peripheral region 322 that includes, in cross section, a counter taper that is configured to reduce glare from light incident on optic 302. The counter taper may have an angle from the horizontal plane that is from −3 degrees to −7 degrees. Thus, the angle formed in cross section at the juncture of peripheral region 322 and other portions of the adjacent optic 302 surface is less than 180 degrees.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An accommodating intraocular lens, comprising:
   an optic disposed about an optical axis including an anterior surface and a posterior surface defining a clear aperture of the optic and defining an optic plane therebetween that is substantially perpendicular to the optical axis;
   a haptic at least partially disposed inside the optic comprising:
      an inner structure circumferentially disposed about the optical axis and lying substantially within the optic plane;
      an outer structure circumferentially disposed about the inner structure and lying substantially within the optic plane; and
      a plurality of arms disposed between and connecting the inner structure and the outer structure, each arm having a proximal portion adjacent the inner structure and a distal portion adjacent the outer structure that is bifurcated in a radial direction from the proximal portion;
   the inner structure disposed inside the clear aperture;
   the distal portion of each arm having a larger axial extent than an axial extent of the inner portion; and
   the distal portion of each arm having a larger axial extent than the outer structure.

2. The intraocular lens of claim 1, wherein the distal portion of each arm comprises a first arcuate portion and a second arcuate portion, the first and second arcuate portions having an axial extent in the anterior and posterior directions.

3. The intraocular lens of claim 2, wherein the first and second arcuate portions at least partially bound an opening.

4. The intraocular lens of claim 1, wherein the inner structure is comprised of a continuous ring about the optical axis.

* * * * *